United States Patent [19]

Churchman

[11] 4,182,159
[45] Jan. 8, 1980

[54] PRESSURE TESTING TOOL
[75] Inventor: Ronald K. Churchman, Plano, Tex.
[73] Assignee: Otis Engineering Corporation, Dallas, Tex.
[21] Appl. No.: 930,021
[22] Filed: Aug. 1, 1978
[51] Int. Cl.² ............................................. G01M 3/28
[52] U.S. Cl. ................................... 73/40.5 R; 73/49.5
[58] Field of Search .................. 73/40.5 R, 49.1, 49.5, 73/49.8

[56] References Cited
U.S. PATENT DOCUMENTS

| | | | |
|---|---|---|---|
| 2,953,919 | 9/1960 | Potts | 73/49.1 X |
| 2,963,092 | 12/1960 | Anderson et al. | 73/40.5 R X |
| 3,048,998 | 8/1962 | Gilreath | 73/49.1 X |
| 3,412,790 | 11/1968 | Brown | 73/40.5 R X |
| 3,420,095 | 1/1969 | Brown et al. | 73/40.5 R |
| 3,523,580 | 8/1970 | Lebourg | 73/40.5 R X |
| 3,638,723 | 2/1972 | Carroll | 166/215 |
| 4,046,006 | 9/1977 | Dufrene | 73/151 |
| 4,081,990 | 4/1978 | Chatagnier | 73/40.5 R |
| 4,083,230 | 4/1978 | Rome et al. | 73/40.5 R |

OTHER PUBLICATIONS

*Otis Pumpdown Completion Equipment & Service Catalog,* Otis Engineering Corp., Dallas, Tx., Jan. 1978.

Primary Examiner—Gerald Goldberg
Assistant Examiner—Joseph W. Roskos
Attorney, Agent, or Firm—Thomas R. Felger

[57] ABSTRACT

A tool for pressure testing flow conductors. The tool can engage the inside wall of a flow conductor at any location and form a pressure barrier to allow hydrostatic testing of the flow conductor on one side of the tool for leaks. The tool can be used to test either vertical or horizontal flow conductors. The tool is particularly adapted for use with pumpdown or through the flowline (TFL) servicing equipment for hydrostatic testing of tubing in wells. The tool is initially inserted into the flow conductor in a retracted condition. The tool can be moved through the conductor as desired until activated at a selected position within the flow conductor.

17 Claims, 8 Drawing Figures

PRESSURE TESTING TOOL

BACKGROUND OF THE INVENTION

1. Field of the Invention

The present invention relates generally to tools for interior hydrostatic pressure testing of tubing, pipe, and other flow conductors. The present invention is particularly useful for interior hydrostatic pressure testing of tubing contained within a well serviced by pumpdown or through the flowline (TFL) equipment. In order to economically maintain and repair long flow conductors such as tubing in a well, it is important to locate any leaks prior to beginning a maintenance evolution. The pressure testing tool can move easily through a flow conductor until activated. Once activated, the present invention can be positioned at any desired location in the flow conductor and the flow conductor above the tool can be pressure tested. By activating the tool at one end of the flow conductor, pressure tests can be made as the tool is moved towards the other end of the flow conductor. In this manner, any leaks from the interior of the flow conductor can be located.

2. Description of the Prior Art

Interior hydrostatic testing of flow conductors such as tubing and pipe is well known. A common practice prior to inserting tubing into a well bore is to pressure test the tubing string as it is made up on the working platform. Also, most regulatory agencies require extensive hydrostatic pressure testing of pipelines before the pipeline can be placed into service.

U.S. Pat. No. 4,046,006 to A. Dufrene discloses a tubing plug apparatus for use in pressure testing well tubing. The plug apparatus is limited to wells which can be serviced by conventional wireline techniques. Also, the plug apparatus can be used only in tubing strings which have an interior collar recess for engagement by the plug.

U.S. Pat. No. 4,081,990 to J. C. Chatagnier discloses a hydraulic pipe testing apparatus which is adapted to test the joint between two sections of pipe for a leak. The testing apparatus has two packing elements which seal off on either side of the joint to be tested. Hydrostatic test fluid is injected between the two packing elements to check for leakage from the joint. The testing apparatus can not be used to test long lengths of pipe above the apparatus but only short lengths between the packing elements.

U.S. Pat. No. 4,083,230 to D. J. Rome, et al, discloses a tubing testing tool. Hydrostatic test fluid is injected between two packing elements to check for leaks in short lengths of pipe only. The testing tool also requires a separate conduit from the well surface to the tool to supply hydrostatic test pressure.

U.S. Pat. No. 3,638,723 to A. W. Carroll discloses a locator device which is activated by a reduced inside diameter portion of a well flow conductor. U.S. Pat. No. 3,638,723 does not disclose any mechanism to seal off the flow conductor for pressure testing. Also, the locator device, when activated, can only be secured in recesses in the flow conductor such as a landing nipple or collar recess.

The pressure testing tool of the present invention can be used in either vertical or horizontal flow conductors to test long sections for leakage. Although the present invention can be adapted for use with standard wireline equipment, it is particularly useful for TFL serviced wells which do not have vertical access. The pressure testing tool, when activated, can form a pressure barrier at any desired location within the flow conductor without having to engage a recess such as a landing nipple or collar recess between sections of the flow conductor.

SUMMARY OF THE INVENTION

The present invention is a tool for pressure testing flow conductors comprising a mandrel means, a packing element carried on the exterior of said mandrel means, a flow passage through said mandrel means having openings on either side of said packing element, a check valve contained within said flow passage blocking fluid flow in one direction and allowing fluid flow in the other direction, means for expanding said packing element to form a seal between said mandrel means and said flow conductor, and means for securing said tool at a desired location within said flow conductor.

One object of the present invention is to provide a tool for pressure testing flow conductors which can engage the flow conductor at any desired location and form a pressure barrier within the flow conductor.

Another object of the present invention is to provide a tool for pressure testing flow conductors which can be easily moved through the flow conductor until activated within the flow conductor.

Still another object of the present invention is to provide a tool for pressure testing flow conductors which can be used when the flow conductor is in either a vertical or horizontal position.

A further object of the present invention is to provide a tool for pressure testing flow conductors which can be adapted for use with conventional wireline equipment or with pumpdown equipment.

Another object of the present invention is to provide a tool for pressure testing flow conductors which can be inserted into well tubing by pumpdown techniques, activated at a desired position within the tubing, engage the tubing and form a pressure barrier to allow hydrostatic pressure testing of the tubing above the tool.

Other objects and advantages of the present invention will become readily apparent to those skilled in the art from reading the following description in conjunction with the accompanying drawings illustrating various embodiments of the present invention.

DESCRIPTION OF THE PREFERRED EMBODIMENTS

Figure 1A:
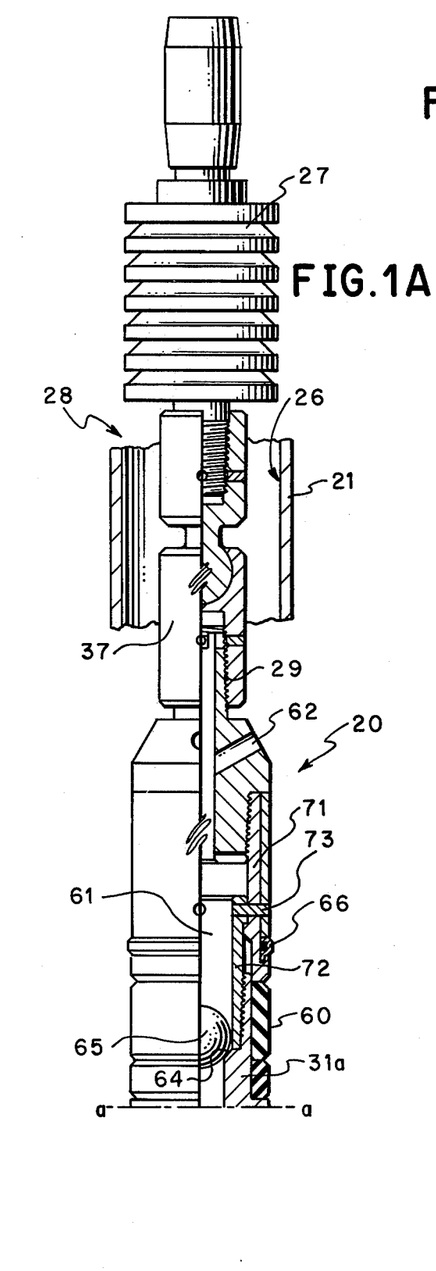
FIG. 1A, partially in section and partially in elevation, shows a portion of the mandrel means carrying the packing element disposed within a well tubing string.
Figure 1B:
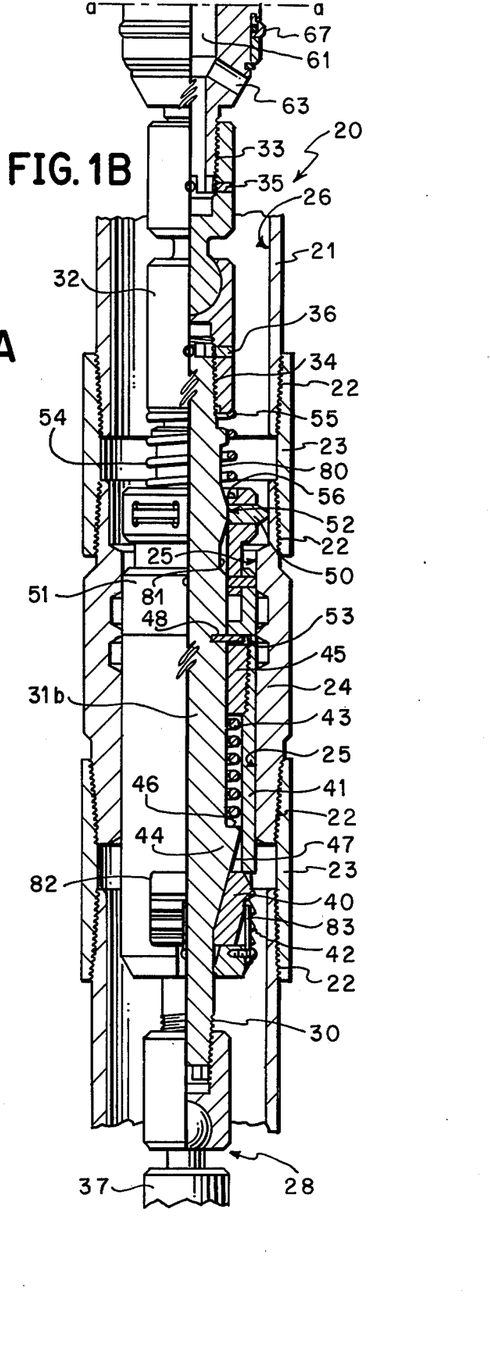
FIG. 1B, partially in section and partially in elevation, shows a portion of the mandrel means carrying the slips in an initially retracted position within a well tubing string.

Referring to the drawings and specifically to FIGS. 1A and 1B, the pressure testing tool of the present invention is generally designated by the reference numeral 20. Pressure testing tool 20 is shown as disposed within tubing string 21. As will be apparent from the written description and the drawings, tool 20 could be operated in either a vertical or horizontal flow conductor. For the purposes of this written description, the operation of tool 20 will be described with respect to a vertical well tubing string.

Tubing string 21 is disposed within a typical well casing (not shown) and communicates a producing formation (not shown) to a well head (not shown). A typical tubing string 21 includes threaded connections 22, collars 23 and landing nipples 24. A landing nipple is placed within the tubing string to provide a location for securing flow control devices such as subsurface safety valves or bean chokes within the tubing string. Landing nipple 24 has a reduced inside diameter 25 which is smaller than the inside diameter 26 of the remainder of the tubing string. The number of landing nipples located within a given tubing string depends upon the complexity of the well completion, the number of producing formations, and the anticipated method of production late in the well life.

Pressure testing tool 20 is shown in FIGS. 1A and 1B in an inert or retracted position such that the outside diameter of tool 20 is compatible with normal tubing inside diameter 26. Therefore, pressure testing tool 20 can be moved through the tubing string by either wireline or pumpdown techniques. As shown in FIGS. 1A and 1B, pressure testing tool 20 is positioned within the tubing string by pumpdown locomotive 27. A detailed description of pumpdown locomotives and the makeup of a pumpdown tool string is given in the Otis Engineering Corporation *Pumpdown Completion Equipment and Service Catalog* published in January, 1978 (OEC5113A) page 32. Pressure testing tool 20 has connecting means 28 at either end for attaching the tool to a standard pumpdown tool string. The connecting means 28 consists of knuckle joints 37 which are connected by threads 29 to the upper end of the tool and threads 30 to the lower end of the tool.

As shown in FIGS. 1A and 1B, tool 20 includes a mandrel means having a first section 31b and a second mandrel section 31a connected by knuckle joint 32. As will be explained later, tool 20 can be constructed on a continuous mandrel or an articulating mandrel as shown in FIGS. 1A and 1B. Knuckle joint 32 is connected to second section 31a by threads 33 and to first section 31b by threads 34. Roll pin 35 prevents threaded connection 33 from becoming disengaged and roll pin 36 prevents threaded connection 34 from becoming disengaged.

First mandrel section 31b carries means for securing tool 20 at any desired location within tubing 21 comprising slips 40 and conical section 44. Slips 40 are carried in windows 82 of housing 41 slidably mounted on first mandrel section 31b. Slips 40 can be expanded radially from the mandrel means through windows 82 in housing 41 to engage the inner wall 26 of tubing 21 at any desired location after the slip biasing means has been activated. Slips 40 include teeth 42 which prevent movement of tool 20 in one direction within the tubing string but allow movement of tool 20 in the other direction within the tubing string even though the slips are expanded from the mandrel means. First mandrel section 31b carries biasing means comprising spring 43, conical section 44 and spring stop 45 engaged with housing 41. When the biasing means is activated, spring 43, resting on shoulder 46 of conical section 44, urges spring stop 45 and housing 41 longitudinally which slides slips 40 over the sloped surface 47 of conical section 44 and expands slips 40 radially from the mandrel means. A resilient means such as leaf spring 83 has one end secured to housing 41 and the other end resting on slips 40. Spring 83 urges slips 40 to remain in close contact with mandrel section 31b.

The biasing means for slips 40 are held in an inert or inactive position by shear means 48. With slips 40 in the retracted position first mandrel section 31b will pass freely through the bore of the tubing string in either direction. First section 31b also carries means for releasing the biasing means at a selected position within the tubing string. The releasing means includes dog means 50 which are normally retained by carrier 51 on an enlarged diameter portion 52 of first section 31b. When dogs 50 are resting on the enlarged diameter portion 52, the outside diameter of tool 20 is such that the tool will pass freely through the bore of the tubing but will not freely pass through reduced inside diameter 25 within landing nipple 24. Carrier 51 acts as a retainer housing to maintain dogs 50 in contact with mandrel section 31b. The lower end of carrier 51 has a shoulder 53 which contacts shear mechanism 48 and housing 41 when dogs 50 are resting on enlarged diameter portion 52. As will be explained later, dogs 50 and carrier 51 comprise part of the means for releasing shear mechanism 48 to activate the slip biasing means. First section 31b carries a second spring 54 with one end 55 resting on the knuckle joint 32 and the other end 56 abutting carrier 51. Spring 54 urges dogs 50 to rest on enlarged diameter 52.

Second mandrel section 31a carries sealing means 60, formed from elastomeric material of suitable qualities, in a normally retracted position. When packing or sealing means 60 is expanded a fluid tight seal is formed between mandrel section 31a and the inside diameter 26 of tubing 21. A flow passage 61 is formed within mandrel section 31a with openings 62 and 63 on either side of packing means 60. Flow passage 61 provides a means for fluid to communicate from below packing means 60 to above packing means 60. A check valve seat 64 is formed within flow passage 61. A ball element 65 contained within flow passage 61 cooperates with seat 64 to restrict flow through passage 61 in one direction and to allow flow through passage 61 in the other direction. In this manner, ball 65 and seat 64 cooperate with packing element 60 to provide a pressure barrier for pressure testing the tubing string above tool 20. Second mandrel section 31a carries centralizers 66 and 67 which have an outside diameter larger than the remainder of second mandrel section 31a when packing element 60 is retracted. The centralizers maintain mandrel 31 a uniform distance from the inside diameter 26 of the tubing string 21 when the packing element is retracted. Preferably centralizers 66 and 67 are constructed of a hard material such as 17-4 PH stainless steel to minimize wear. The centralizers protect the packing element from wear while moving tool 20 through the flow conductor.

Second mandrel section 31a carries means for expanding packing element 60 including telescoping sections 71 and 72. Shear pin 73 releasably holds the telescoping sections in an extended position. When slips 40 are expanded to engage the tubing inside diameter 26, increased pressure on locomotive 27 will apply force to telescoping section 71 to shear pin 73. Section 71 will telescope or collapse relative to section 72 and thereby expand packing element 60 to form a fluid seal between the inner wall 26 of tubing string 21 and the exterior of mandrel section 31a.

Operating Sequence

Figure 4A:
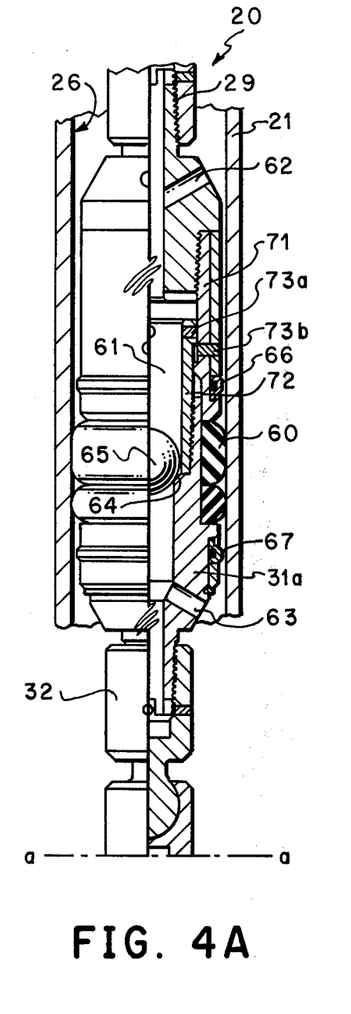
FIG. 4A, partially in section and partially in elevation, shows the tool with the packing element expanded to engage the inner wall of the well tubing to form a pressure barrier for internal hydrostatic pressure testing of the tubing above the tool.
Figure 4B:
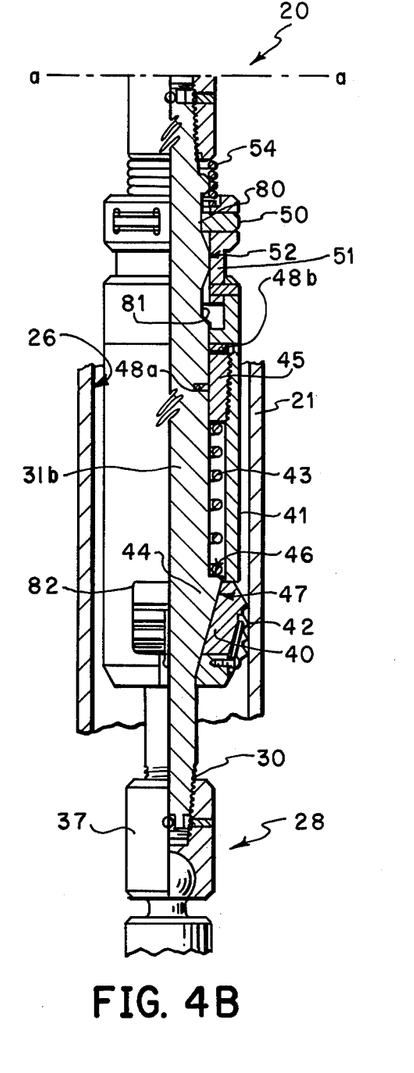
FIG. 4B, partially in section and partially in elevation, shows the tool with the slips engaged with the inner wall of the well tubing to prevent movement of the tool in one direction within the tubing.

As shown in FIGS. 1A and 1B, pumpdown fluid pressure can be applied to locomotive 27 to move tool 20 through tubing string 21 in either direction since slips 40 are retracted. Pumpdown fluid pressure from below tool 20 can be applied to locomotive 27 to move tool 20 in the other direction within tubing string 21 when slips 40 are expanded as shown in FIG. 4B. As best shown in FIG. 1B, dogs 50 can not pass freely through reduced inside diameter 25 while dogs 50 are resting on enlarged diameter portion 52 of mandrel section 31b.

Figure 2:
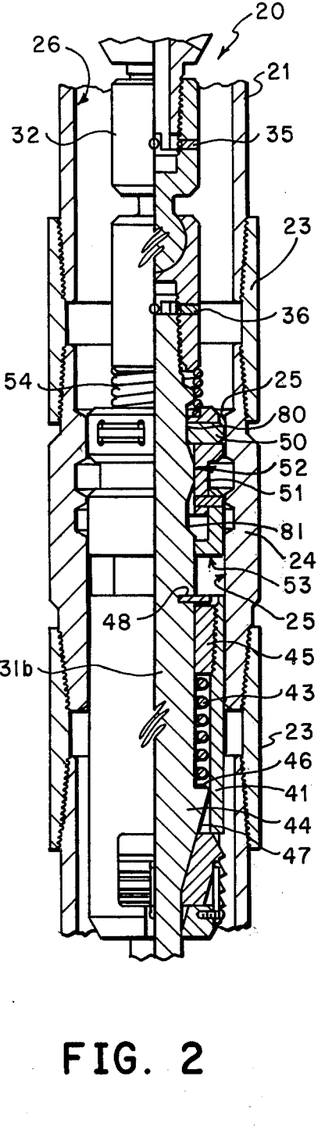
FIG. 2, is a view similar to FIG. 1B showing the tool entering a portion of the well tubing string having a reduced inside diameter.

When tool 20 moves in one direction through a reduced inside diameter portion 25 of tubing 21, dogs 50 will engage the reduced inside diameter. Continued pressure in the one direction applied to locomotive 27, will result in dogs 50 moving carrier 51 in the other direction relative to mandrel section 31b and compressing spring 54. As best shown in FIG. 2, dogs 50 can retract inside a recess 80 above enlarged diameter portion 52 in mandrel section 31b. With dogs 50 in recess 80, tool 20 can pass through the reduced inside diameter 25. Spring 54 returns tool 20 to its initial condition as shown in FIG. 1B after tool 20 has moved through the restriction in tubing 21. In this manner, tool 20 can be pumped through a flow conductor in the one direction with any number of restrictions without activating the slip biasing means.

When tool 20 reaches the desired position within tubing 21 to activate the slip biasing means, pumpdown fluid pressure from the other direction is applied to locomotive 27 to move tool 20 in the other direction.

Figure 3:
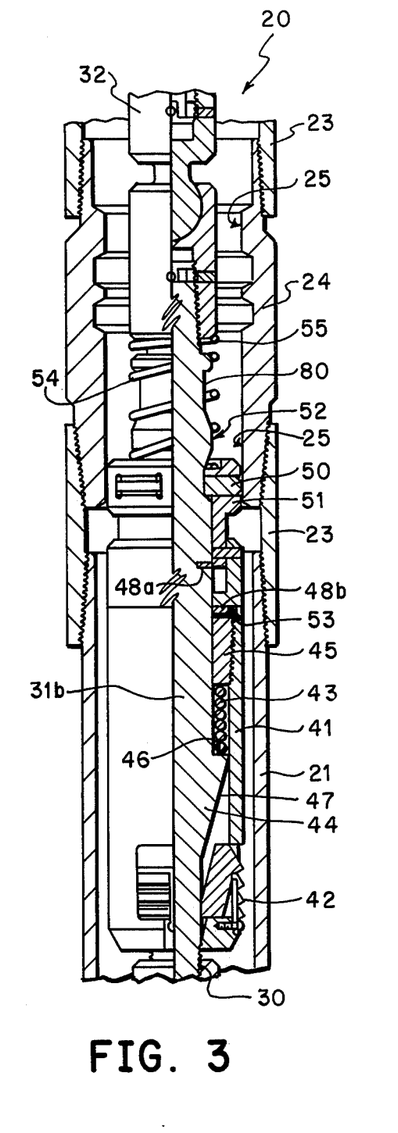
FIG. 3, is a view similar to FIG. 2 showing the tool moving upwards through a reduced inside diameter portion of the well tubing to activate the slip biasing means.

As tool 20 moves in the other direction through a restriction or reduced inside diameter portion 25, dogs 50 will engage the restriction. Shear pin 48 prevents carrier 51 from moving in the one direction relative to mandrel section 31b. Continued pressure on locomotive 27 will cause shoulder 53 on carrier 51 to shear pin 48 and allow carrier 51 to move in the one direction relative to mandrel section 31b. As best shown in FIG. 3, the slip biasing means is activated by moving tool 20 upward through a restriction such as nipple 24. Pin 48 is sheared into two pieces 48a and 48b allowing dogs 50 to slide into recess 81. Tool 20 can then move freely through the reduced inside diameter in tubing 21.

If tool 20 was being used to test a horizontal flow conductor, it would still be moved in one direction with the slips retracted. Movement in the other direction through a restriction or reduced inside diameter in a horizontal flow conductor would activate the slip biasing means.

As tool 20 moves in the other or upward direction out of nipple 24, spring 43 will move spring stop 45, housing 41 and carrier 51 in the other direction relative to mandrel section 31b. Spring 43 must be stronger than spring 54 to properly activate the slip biasing means. As shown in FIG. 4B, spring 43 can overcome spring 54 to move dogs 50 from recess 81 to recess 80 when tool 20 is free from the restriction within tubing 21. Also, spring 43 moves housing 41 in the other direction relative to mandrel section 31b and expands slips 40 outward through window 82 in housing 41. Tool 20 can be moved in the other direction through tubing 21 with slips 40 dragging against the inside tubing wall. Pressure on locomotive 27 in the one direction, when the slip biasing means is activated, would result in surface 47 on conical section 44 forcing slips 40 outward to secure tool 20 within the flow conductor. In this manner tool 20 is prevented from moving in the one direction within tubing 21. Tool 20 can move in the other direction within tubing 21 even though the slip biasing means has been activated.

With slips 40 engaging tubing 21, fluid pressure on locomotive 27 can not move tool 20 downward or in the one direction within tubing 21. As the fluid pressure is increased, pin 73 in second mandrel section 31a will shear, releasing telescoping section 71 from section 72. Since slips 40 are holding mandrel section 31b in place and telescoping section 72 can not move relative to mandrel section 31b, telescoping section 71 will move in the one direction expanding packing element 60 into sealing engagement with tubing 21. FIG. 4A shows packing element 60 expanded, pin 73 sheared into pieces 73a and 73b, and telescoping section 71 spaced longitudinally from section 72. Ball element 65 is shown engaged with check valve seat 64. Therefore, packing element 60 and ball 65 cooperate to form a pressure barrier to allow interior hydrostatic pressure testing of the tubing above tool 20.

After the slip biasing means is activated, tool 20 can be moved in the other direction within tubing 21 until reaching a desired location for hydrostatic pressure testing. The direction of fluid pressure moving tool 20 is reversed to cause slips 40 to engage the tubing and to expand packing element 60 to form a pressure barrier. Fluid pressure can be applied by pumpdown techniques to move tool 20 in the other direction within tubing 21 after the first hydrostatic test is completed. When tool 20 reaches the next desired position for hydrostatic pressure testing, the direction of fluid pressure moving tool 20 is reversed and the above steps repeated. In this manner, a flow conductor of any length can be tested at various locations while moving tool 20 from one end to the other end of the flow conductor.

Tool 20 can be adapted for engagement with a standard wireline tool string for raising and lowering tool 20 within tubing 21. When using wireline, a device similar to locomotive 27 must be used to receive fluid pressure from the well surface to expand slips 40 and packing element 60.

Alternative Embodiments

Figure 5:
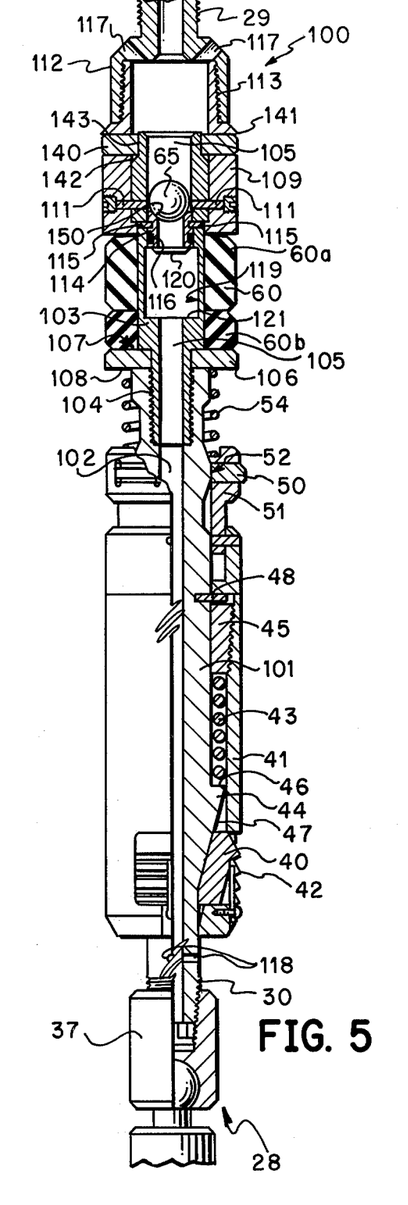
FIG. 5, partially in section and partially in elevation, shows an alternative embodiment of the present invention in which the check valve can be released from a position blocking flow through the interior of the mandrel means. Also, the mandrel means does not contain an articulating section between the slips and the packing element.

The mandrel means for the pressure testing tool as shown in FIGS. 1A and 1B consists of a first section 31b and a second section 31a with a knuckle joint 32 joining the two sections. For some applications, it may be desirable to use a tool having a continuous mandrel as shown in FIG. 5.

A modified pressure testing tool is indicated generally by reference numeral 100 with means for connecting tool 100 to a pumpdown or wireline tool string such as threads 29 and 30 at either end thereof. Tool 100 comprises a lower mandrel section 101 having a longitudinal flow passage 102. Section 101 carries slips 40, dogs 50, carrier 51, housing 41 and springs 43 and 54 which function in the same manner as previously described for the embodiment shown in FIG. 1B.

Tool 100 also comprises an upper section 103 which is connected to lower section 101 by threads as at 104 within flow passage 102. Upper mandrel section 103 contains a longitudinal flow passage 105 which is aligned with flow passage 102 when sections 101 and 103 are engaged. Support disc 106 is secured between lower section 101 and upper section 103 while making up threaded connection 104. Upper surface 107 of disc 106 provides a support for expanding packing elements 60. Lower surface 108 of disc 106 provides a support for one end of spring 54 to urge dogs 50 to rest on the enlarged diameter portion 52 of lower section 101.

Packing or sealing element 60 comprises two cylindrical portions 60a and 60b which are carried on the exterior of upper section 103. Packing element 60 is formed from elastomeric material which can be compressed against support disc 106 and expanded to form a seal between a flow conductor inner wall (not shown) and the exterior of upper section 103.

Compression cylinder 109 surrounds upper section 103 with packing element 60 disposed between bottom surface 110 of cylinder 109 and support disc 106. Cylinder 109 is releasably engaged with section 103 by shear pins 111. Adapter head 112 is connected to the upper end of compression cylinder 109 by threads 113. Adapter head 112 also has means such as threads 29 for connecting tool 100 to a pumpdown or wireline tool string. With a means for applying force to adapter head 112 such as locomotive 27 shown in FIG. 1A, pin 111 can be sheared by applying fluid pressure to the interior of the flow conductor when slips 40 are biased to engage the flow conductor. With pin 111 sheared, a force applying means such as locomotive 27 and adapter head 112 can move compression cylinder 109 towards support disc 106 and expand packing element 60 to form a pressure barrier within the flow conductor for hydrostatic testing of the flow conductor.

In order for packing element 60 to establish a satisfactory seal with the flow conductor, tool 100 should preferrably be spaced an equal distance from the inner wall of the flow conductor while expanding packing element 60. Compression cylinder 109 has windows 141 opening radially through cylinder 109 and near the upper end of mandrel section 103. A centralizer 140 is disposed within each window 141 and rests on a reduced diameter portion 143 of mandrel section 103 when packing element 60 is retracted. Reduced diameter portion 143 and centralizer lugs 140 are sized such that lugs 140 do not project from tool 100 when compression cylinder 109 is extended longitudinally from support disc 106. A cam surface 142 is formed on the exterior of mandrel section 103 adjacent reduced diameter portion 143. Movement of compression cylinder 109 toward disc 106 will cause centralizer 140 to slide over cam surface 142 and project radially through window 141. Tool 100 will thus be spaced an equal distance from the inner wall of the flow conductor by projecting centralizers 140 radially while expanding packing element 60.

In addition to packing element 60 the pressure barrier also comprises a check valve disposed within flow passage 105 to prevent flow in one direction and to allow flow in the other direction. Any suitable check valve could be used. As shown in FIG. 5, a valve seat 114 is releasably secured to the inner wall of mandrel section 103 by shear pin 115. O ring 116 is carried on the exterior of valve seat 114 and forms a fluid tight seal between seat 114 and the inner wall of upper section 103 when shear pins 115 are installed. Ball member 65 is disposed within flow passage 105 and can rest on seat surface 150 formed on valve seat 114 and the inner wall of upper section 103 when shear passage 105. Flow in the other direction through passage 105 will lift ball 65 from seat surface 150.

As previously explained when upper section 103 is engaged with lower section 101, flow passage 102 and 105 are aligned to allow fluid communication. Adapter head 112 has ports 117 which allow fluid from above packing element 60 to communicate with flow passage 105. Lower section 101 contains ports 118 which allow fluid communication from below packing element 60 to flow passage 102.

Generally, when slips 40 are biased to engage the flow conductor, it is not necessary to pump fluid in the one direction past tool 100. However, during some well conditions, it may be desirable to communicate fluid in both directions through tool 100. Flow passage 105 has an enlarged bore 119 adjacent valve seat 114 and opposite ball 65. If the fluid pressure forcing ball 65 and seat surface 150 into sealing engagement exceeds a preselected value, pin 115 will shear allowing valve seat 114 to move into enlarged bore 119. O ring 116 can not seal with enlarged bore 119. Therefore, fluid can communicate in either direction through passageway 105. Valve seat 114 has a rib 120 to prevent the lower end of seat 114 from forming a metal face seal with shoulder 121 in bore 119.

Figure 6:
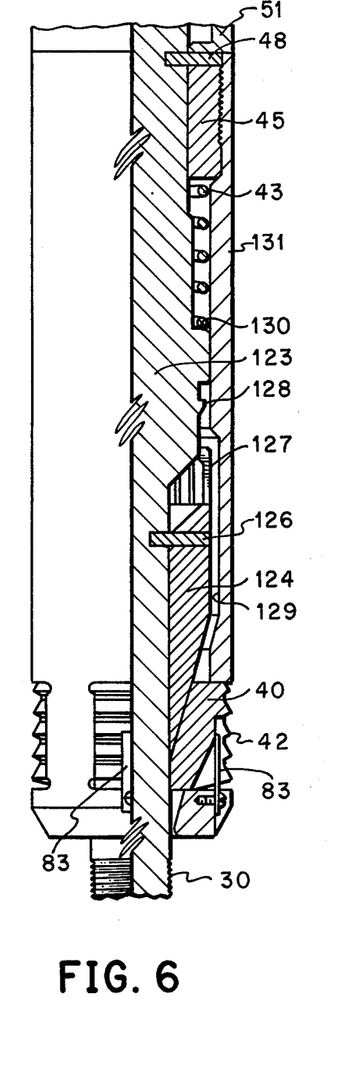
FIG. 6, is a fragmentary view in enlarged scale to show an alternative embodiment of the present invention having means for releasing the slips from the tubing inner wall and for allowing the tool to move in the one direction after the slip biasing means has been activated.

FIG. 6 shows another alternative embodiment of the present invention. When dogs 50 and carrier 51 have activated the slip biasing means by shearing pin 48, slips 40 will engage the flow conductor to prevent movement of the pressure testing tool in the one direction within the flow conductor. However, under some conditions it may be desirable to be able to move the pressure testing tool in either direction after the biasing means has been activated.

Referring to FIG. 6, conical section 124 is releasably engaged in a first position with lower mandrel section 123 by shear pin 126. Spring means 43 does not rest on the conical section as shown in FIG. 1B but rather on a separate shoulder 130 formed on lower mandrel section 123. When pin 48 is sheared, spring means 43 will move spring stop 45 and housing 131, attached to stop 45, longitudinally with respect to mandrel 123. Housing 131 will slide slips 40 over conical section 124 and expand slips 40 radially from mandrel 123 as long as conical section 124 is in its first position. With the biasing means activated, hydrostatic pressure testing of the flow conductor can be accomplished as previously described.

If it is necessary to move the pressure testing tool in the one direction after the slips have been expanded radially, fluid pressure is increased to a preselected value to shear pin 126 and release conical section 124 from mandrel 123. Flexible collet fingers 127 formed on conical section 124 can engage flange or catch 128 formed on mandrel 123 as mandrel 123 moves longitudinally relative to conical section 124. This will then hold conical section 124 in its second position. Housing 131 has an internal recess 129 to allow collet fingers 127 to flex radially while engaging flange 128. The direction of fluid pressure is reversed after latching the collet fingers 127 to pull conical section 124 in its second position. Resilient means or leaf spring 83 can then return slips 40 to their initial retracted position. The free end length of spring 43 is sized such that spring 43 can not bias housing 131 to slide slips 40 over conical section 124 when collet fingers 127 are engaged with flange 128. Therefore, the well pressure testing tool can be moved in either direction within the flow conductor after pin 126 has been sheared and conical section 124 is held in its second position.

The present invention can be used to conduct an interior hydrostatic pressure test of various types of flow conductors. The previous description is illustrative of only some of the embodiments of the invention. Those skilled in the art will readily see other variations for a pressure testing tool utilizing the present invention. Changes and modifications may be made without departing from the scope of the invention which is defined by the claims.

What is claimed is:

1. A tool for pressure testing flow conductors, comprising:
    a. mandrel means;
    b. means, carried on the exterior of said mandrel means, for sealing between said mandrel means and said flow conductor;
    c. a flow passage through said mandrel means having openings on either side of said sealing means;
    d. a check valve contained within said flow passage blocking fluid flow in one direction and allowing fluid flow in the other direction;
    e. means for expanding said sealing means;
    f. slips carried by said mandrel means in an initially retracted position;
    g. means for biasing said slips to an expanded position to engage said flow conductor whereby movement of said tool in said one direction is prevented and movement of said tool in said other direction is allowed;
    h. means for holding said slip biasing means in an inert condition until activated; and
    i. said means for expanding said sealing means further comprising telescoping sections on said mandrel adjacent to said sealing means, means for releasably holding said telescoping sections in an extended position, and means for applying a force to one of said telescoping sections when said slips are engaged with said flow conductor, whereby said releasable holding means are overcome and said telescoping sections move to a position expanding said sealing means to engage said flow conductor.

2. A tool for pressure testing flow conductors as recited in claim 1, wherein said means for biasing said slips further comprises:
    a. conical section formed on said mandrel adjacent to said slips;
    b. a housing slidably holding said slips on said mandrel;
    c. a first spring with one end engaging said mandrel and the other end engaging said housing, said first spring urging said housing to slide said slips over said conical section and extend said slips from said mandrel; and
    d. a shear mechanism engaging said mandrel and said housing to hold said first spring in an inert position with said slips retracted against said mandrel.

3. A tool for pressure testing flow conductors as recited in claim 2, further comprising:
    means for releasing said shear mechanism at a desired location within said flow conductor and allowing said biasing means to expand said slips.

4. A tool for pressure testing flow conductors as recited in claim 2, further comprising:
    resilient means attached to said housing and engaging said slips to urge said slips into said retracted position.

5. A tool for pressure testing flow conductors as recited in claim 2, wherein said conical section further comprises:
    a. means for releasing said conical section from a first position on said mandrel when said slips are expanded; and
    b. means for engaging said conical section in a second position on said mandrel to prevent said slips from moving over said conical section.

6. A tool for pressure testing flow conductors as recited in claim 1, further comprising:
    a. an enlarged diameter portion on said mandrel having a recess on either side thereof;
    b. dog means normally resting on said enlarged diameter portion and extending radially from said mandrel, said dog means being sized to prevent movement of said tool through a reduced inside diameter portion of said flow conductor when said dog means are resting on said enlarged diameter portion;
    c. a carrier slidably holding said dog means on said mandrel and size to contact said means for biasing said slips when said dog means are resting on said enlarged diameter portion;
    d. a second spring with one end engaging said mandrel and the other end engaging said carrier and urging said dog means to rest on said enlarged diameter portion whereby movement of said tool in one direction through a reduced inside diameter portion within said flow conductor causes said second spring to compress and said carrier to slide said dog means into a recess on said mandrel until said tool has moved through said reduced inside diameter portion and movement of said tool in the other direction through said reduced inside diameter to activate said means for biasing said slips and to expand said slips from said mandrel.

7. A tool for pressure testing flow conductors as recited in claim 1, wherein said check valve further comprises:
    a. a valve seat releasably secured within said flow passage;
    b. a seat surface formed on said valve seat;
    c. a ball means disposed within said flow passage and engagable with said seat surface to block fluid flow in said one direction through said flow passage; and
    d. means for releasing said valve seat from said flow passage at a preselected fluid pressure to allow flow in either direction through said flow passage.

8. A tool for pressure testing flow conductors comprising:
    a. a first mandrel section;
    b. slips carried by said first mandrel section in an initially retracted position;

c. means for biasing said slips to an expanded position from said first mandrel section;
d. said slips having means for engaging said flow conductor when expanded from said first mandrel to prevent movement of said tool in one direction and to allow movement of said tool in the other direction within said flow conductor;
e. means for holding said slip biasing means in an inert condition until activated at a desired location within said flow conductor;
f. a second mandrel section having a longitudinal flow passage therethrough and connected to said first mandrel section;
g. a check valve disposed within said flow passage in said second mandrel section, said check valve allowing fluid flow through said flow passage in said other direction and preventing fluid flow through said flow passage in said one direction;
h. a sealing element carried on the exterior of said second mandrel;
i. means for expanding said sealing element to form a seal between said second mandrel section and said flow conductor;
j. an enlarged diameter portion on said first mandrel section having a recess on either side thereof;
k. dogs normally resting on said enlarged diameter portion and extending therefrom, said dogs being sized to prevent movement of said tool through a reduced inside diameter portion of said flow conductor when said dogs are resting on said enlarged diameter portion;
l. a carrier slidably holding said dogs on said mandrel and sized to contact said means for biasing said slips when said dogs are resting on said enlarged diameter portion; and
m. means for urging said carrier to contact said biasing means and said dogs to rest on said enlarged diameter portion whereby movement of said tool in one direction through a reduced inside diameter portion of said flow conductor causes said dogs to slide into a recess on said first mandrel section until said tool has moved through said reduced inside diameter portion of said flow conductor and movement of said tool in said other direction through said reduced diameter portion causes said carrier to activate said means for biasing said slips.

9. A tool for pressure testing flow conductors as recited in claim 8, wherein said means for expanding said sealing element further comprises:
a. telescoping sections on said second mandrel section adjacent to said sealing element;
b. means for releasably holding said telescoping sections in an extended position; and
c. means for applying a force to one of said telescoping sections when said slips are engaged with said flow conductor, whereby said releasable holding means are overcome and said telescoping sections move to a retracted position expanding said sealing element to engage said flow conductor.

10. A tool for pressure testing flow conductors as recited in claim 8, wherein said means for biasing said slip further comprises:
a. a conical section formed on said first mandrel section adjacent to said slips;
b. a housing slidably holding said slips on said first mandrel section;
c. a spring with one end engaging said first mandrel and the other end engaging said housing, said spring urging said housing to slide said slips over said conical section and extend said slips from said first mandrel;
d. a shear mechanism engaging said first mandrel section and said housing to hold said spring in a compressed position with said slips retracted against said first mandrel section.

11. A tool for pressure testing flow conductors as recited in claim 10, further comrprising:
a. means for attaching said tool to a locomotive;
b. resilient means attached to said housing and engaging said slips to urge said slips into said retracted position.

12. A tool for pressure testing flow conductors as recited in claim 10, wherein said conical section further comprises:
a. means for releasing said conical section from a first position on said mandrel when said slips are expanded; and
b. means for engaging said conical sections in a second position on said mandrel to prevent said slips from moving over said conical section.

13. A tool for pressure testing flow conductors as reciated in claim 8, wherein said check valve further comprises:
a. a valve seat releasably secured within said flow passage;
b. a seat surface formed on said valve seat;
c. a ball means disposed within said flow passage and engageable with said seat surface to block fluid flow in said one direction through said flow passage;
d. means for releasing said valve seat from said flow passage at a preselected fluid pressure to allow flow in either direction through said flow passage;

14. A tool for pressure testing flow conductors, comprising:
a. a first mandrel;
b. slips carried on said first mandrel by a housing in an initially retracted position, said slips having teeth which can engage said flow conductor to prevent movement of said tool in one direction and to allow movement of said tool in the other direction within said flow conductor.
c. a conical section on said first mandrel adjacent to said slips;
d. means for urging said housing to move relative to said first mandrel and expand said slips radially from said first mandrel over said conical section;
e. a shear mechanism holding said housing and said urging means in said initial position with said slips retracted;
f. means for contacting said shear mechanism to expand said slips, comprising;
dog means normally carried on an enlarged diameter portion of said first mandrel by a carrier, said carrier contacting said sheer mechanism when said dogs are resting on said enlarged portion;
said first mandrel having a first and second recess on either side of said enlarged diameter portion;
a spring having one end supported by said first mandrel and the other end engaging said carrier whereby movement of said dogs into said first recess will compress said spring and movement of said dogs into said second recess will shear said shear mechanism and activate said urging means;

g. a second mandrel coupled to said first mandrel by a knuckle joint;

h. a sealing element carried on the exterior of said second mandrel;

i. a flow passage through said second mandrel having an opening to the exterior of said mandrel on either side of said sealing element;

j. a check valve disposed within said flow passage blocking fluid flow in said one direction and allowing fluid flow in said other direction within said flow passage;

k. said second mandrel including two sections which can telescope relative to each other and expand said sealing element from said second mandrel;

l. a releasable mechanism normally holding said telescoping sections in an extended position with said sealing element retracted against said second mandrel; and m. means for attaching one of said telescoping sections to a force applying means such as a pump-down locomotive whereby said force applying means can expand said sealing element when said slips are engaging said flow conductor.

15. A tool for pressure testing flow conductors as recited in claim 14, wherein said check valve further comprises:

a. a valve seat releasably secured within said flow passage;

b. a seat surface formed on said valve seat;

c. a ball means disposed within said flow passage and engageable with said seat surface to block fluid flow in said one direction through said flow passage;

d. means for releasing said valve seat from said flow passage at a preselected fluid pressure to allow flow in either direction through said flow passage.

16. A tool for pressure testing flow conductors as recited in claim 14, further comprising:

a resilient means attached to said housing and engaging said slips to urge said slips into said retracted position.

17. A tool for pressure testing flow conductors as recited in claim 14, wherein said conical section further comprises:

a. means for releasing said conical section from a first position on said mandrel when said slips are expanded; and b. means for engaging said conical section in a second position on said mandrel to prevent said slips from moving over said conical section.

* * * * *

UNITED STATES PATENT AND TRADEMARK OFFICE
CERTIFICATE OF CORRECTION

PATENT NO. : 4,182,159

DATED : January 8, 1980

INVENTOR(S) : Ronald K. Churchman, Plano, Texas

It is certified that error appears in the above—identified patent and that said Letters Patent is hereby corrected as shown below:

In column 7, line 49,
 "errably" should read --erably--

In column 10, line 35,
 "size" should read --sized--

In column 11, line 62,
 "slip" should read --slips--

In colume 12, line 9,
 "comrprising" should read --comprising--

In column 12, line 24,
 "reciated" should read --recited--

In column 12, line 57,
 "sheer" should read --shear--

Signed and Sealed this

Fifth Day of August 1980

[SEAL]

Attest:

Attesting Officer

SIDNEY A. DIAMOND

Commissioner of Patents and Trademarks